US011518989B1

(12) United States Patent
Davis et al.

(10) Patent No.: US 11,518,989 B1
(45) Date of Patent: Dec. 6, 2022

(54) ENGINEERING RUBISCO FOR FOOD SAFETY

(71) Applicants: National Technology & Engineering Solutions of Sandia, LLC, Albuquerque, NM (US); Arizona Board of Regents on behalf of Arizona State University, Scottsdale, AZ (US)

(72) Inventors: Ryan Wesley Davis, San Jose, CA (US); Joseph S. Schoeniger, Oakland, CA (US); Arul M. Varman, Tempe, AZ (US); Muhammad Faisal, Tempe, AZ (US); Aditya Pandharinath Sarnaik, Tempe, AZ (US)

(73) Assignees: National Technology & Engineering Solutions of Sandia, LLC, Albuquerque, NM (US); Arizona Board of Regents on behalf of Arizona State University, Scottsdale, AZ (US)

( * ) Notice: Subject to any disclaimer, the term of this patent is extended or adjusted under 35 U.S.C. 154(b) by 7 days.

(21) Appl. No.: 17/038,513

(22) Filed: Sep. 30, 2020

(51) Int. Cl.
*C12N 9/88* (2006.01)
*C12N 1/21* (2006.01)
*A23J 1/00* (2006.01)

(52) U.S. Cl.
CPC ........ *C12N 9/88* (2013.01); *C12Y 401/01039* (2013.01)

(58) Field of Classification Search
None
See application file for complete search history.

(56) References Cited

U.S. PATENT DOCUMENTS

| | | | | |
|---|---|---|---|---|
| 4,268,632 | A * | 5/1981 | Wildman | A23J 1/007 435/816 |
| 10,519,204 | B2 * | 12/2019 | Patinier | C07K 1/34 |
| 2001/0032342 | A1 * | 10/2001 | Stemmer | C12N 9/88 800/278 |

FOREIGN PATENT DOCUMENTS

| | | |
|---|---|---|
| EP | 3247795 A1 | 11/2017 |
| EP | 3318624 A2 | 5/2018 |
| JP | 2013180962 A | 9/2013 |
| JP | 2018131414 A | 8/2018 |

OTHER PUBLICATIONS

WHO Technical Report Series 935, Protein and amino acid requirements in human nutrition, Chapter 6: Protein quality evaluation, 2007. (Year: 2007).*
Marcus et al., Activation of cyanobacterial RuBP-carboxylase/oxygenase is facilitated by inorganic phosphate via two independent mechanisms, Eur. J. Biochem. 267, 2000, 5995-6003. (Year: 2000).*
Andersson et al. (Structure and function of Rubisco, Plant Phys. Biochem. 46, 2008, 275-91. (Year: 2008).*
Uniprot, Accession No. P54205, 2019, www.uniprot.org (Year: 2019).*
Liu et al., Effect of growth hormone transgenic Synechocystis on growth, feed efficiency, muscle composition, haematology and histology of turbot, Aquaculture Res. 38, 2007, 1283-92. (Year: 2007).*
Occhialini et al., Transgenic tobacco plants with improved cyanobacterial Rubisco expression but no extra assembly factors grow at near wild-type rates if provided with elevated CO2, Plant J. 85, 2016, 148-60. (Year: 2016).*
Gen Bank, Accession No. KT203393.1,2016, www.ncbil.nlm.nih.gov. (Year: 2016).*
Zhu et al., Improvement of Pest Resistance in Transgenic Tobacco Plants Expressing dsRNA of an Insect-Associated Gene EcR, PLos One 7, 2012, e38572. (Year: 2012).*
Uniprot, Accession No. Q31NB3, 2019, www.uniprot.org. (Year: 2019).*
Uniport, Accession No. P00876, 2019, www.uniprot.org. (Year: 2019).*
Alagarswami, Review on production of mussel seed, CMFRI Bulletin 29, 1980, 22-26. (Year: 1980).*
Grossmann et al., Cultivation and downstream processing of microalgae and cyanobacteria to generate protein-based technofunctional food ingredients, Critical Rev. Food Sci. Nutrition 60, 2020, 2961-89. (Year: 2020).*
Uniprot, Accession No. B1WXH3, 2019, www.uniprot.org. (Year: 2019).*
Yampolsky et al., The Exchangeability of Amino Acids in Proteins, Genetics, 2005, 170: 1459-72. (Year: 2005).*
Jiang, et al., "Preparation and Characterization of Emulsion Gels from Whole Faba Bean Flour", In Foods, MDPI, vol. 9, No. 755, Jun. 7, 2020, 15 pages.

* cited by examiner

*Primary Examiner* — Robert B Mondesi
*Assistant Examiner* — Todd M Epstein
(74) *Attorney, Agent, or Firm* — Eschweiler & Potashnik, LLC; Madelynne J. Farber; Samantha Updegraff

(57) ABSTRACT

A method of improving a ribulose-1,5-bisphosphate carboxylase/oxygenase (RuBisCo) to have a higher protein score is disclosed. The method includes the steps of: making a modified RbcL of the RuBisCo, by, on an RbcL unit of the RuBisCo, either substituting Met for Leu, Phe, Val, or Ile or combinations thereof; substituting Lys for Arg, Thr, or His or combinations thereof; or both of these substitutions. The modified RbcL consequently modifies the RuBisCo and is added to a biomass host where it is stable for homologous recombination. Plastid and nucleus integration was observed. Example RbcL sequences are disclosed with the desirable substitutions. The improved RuBisCo can be used as an improved proteinaceous food source for humans and animals.

17 Claims, 9 Drawing Sheets
Specification includes a Sequence Listing.

SEQUENCE LISTING

```
<160> NUMBER OF SEQ ID NOS: 5

<210> SEQ ID NO 1
<211> LENGTH: 470
<212> TYPE: PRT
<213> ORGANISM: Artificial sequence
<220> FEATURE:
<223> OTHER INFORMATION: Synthetic peptide

<400> SEQUENCE: 1

Met Val Gln Ala Lys Ala Gly Phe Lys Ala Gly Val Gln Asp Tyr Arg
1               5                   10                  15

Leu Thr Tyr Tyr Thr Pro Asp Tyr Thr Pro Lys Asp Thr Asp Leu Leu
                20                  25                  30

Ala Cys Phe Arg Met Thr Pro Gln Pro Gly Val Pro Ala Glu Glu Ala
            35                  40                  45

Ala Ala Ala Val Ala Ala Glu Ser Ser Thr Gly Thr Trp Thr Thr Val
        50                  55                  60

Trp Thr Asp Asn Leu Thr Asp Leu Asp Arg Tyr Lys Gly Arg Cys Tyr
65                  70                  75                  80

Asp Leu Glu Ala Val Pro Asn Glu Asp Asn Gln Tyr Phe Ala Phe Ile
                85                  90                  95

Ala Tyr Pro Leu Asp Leu Phe Glu Glu Gly Ser Val Thr Asn Val Leu
            100                 105                 110

Thr Ser Leu Val Gly Asn Val Phe Gly Phe Lys Ala Leu Arg Ala Leu
        115                 120                 125

Arg Leu Glu Asp Ile Arg Phe Pro Val Ala Leu Ile Lys Thr Phe Gln
    130                 135                 140

Gly Pro Pro His Gly Ile Thr Val Glu Arg Asp Lys Leu Asn Lys Tyr
145                 150                 155                 160
```

```
Gly Arg Pro Leu Leu Gly Cys Thr Ile Lys Pro Lys Leu Gly Leu Ser
            165                 170                 175

Ala Lys Asn Tyr Gly Arg Ala Val Tyr Glu Cys Leu Arg Gly Gly Leu
        180                 185                 190

Asp Phe Thr Lys Asp Asp Glu Asn Ile Asn Ser Gln Pro Phe Met Arg
        195                 200                 205

Trp Arg Asp Arg Phe Leu Phe Val Gln Glu Ala Ile Glu Lys Ala Gln
    210                 215                 220

Ala Glu Thr Asn Glu Met Lys Gly His Tyr Leu Asn Val Thr Ala Gly
225                 230                 235                 240

Thr Cys Glu Glu Met Met Lys Arg Ala Glu Phe Ala Lys Glu Ile Gly
                245                 250                 255

Thr Pro Ile Ile Met His Asp Phe Phe Thr Gly Gly Phe Thr Ala Asn
                260                 265                 270

Thr Thr Leu Ala Arg Trp Cys Arg Asp Asn Gly Ile Leu Leu His Ile
            275                 280                 285

His Arg Ala Met His Ala Val Val Asp Arg Gln Lys Asn His Gly Ile
        290                 295                 300

His Phe Arg Val Leu Ala Lys Cys Leu Arg Leu Ser Gly Gly Asp His
305                 310                 315                 320

Leu His Ser Gly Thr Val Val Gly Lys Leu Glu Gly Glu Arg Gly Ile
                325                 330                 335

Thr Met Gly Phe Val Asp Leu Met Arg Glu Asp Tyr Val Glu Glu Asp
                340                 345                 350

Arg Ser Arg Gly Ile Phe Phe Thr Gln Asp Tyr Ala Ser Met Pro Gly
            355                 360                 365

Thr Met Pro Val Ala Ser Gly Gly Ile His Val Trp His Met Pro Ala
        370                 375                 380

Leu Val Glu Ile Phe Gly Asp Asp Ser Cys Leu Gln Phe Gly Gly Gly
385                 390                 395                 400

Thr Leu Gly His Pro Trp Gly Asn Ala Pro Gly Ala Thr Ala Asn Arg
                405                 410                 415

Val Ala Leu Glu Ala Cys Val Gln Ala Arg Asn Glu Gly Arg Asn Leu
                420                 425                 430

Ala Arg Glu Gly Asn Asp Val Ile Arg Glu Ala Cys Arg Trp Ser Pro
            435                 440                 445

Glu Leu Ala Ala Ala Cys Glu Leu Trp Lys Glu Ile Lys Phe Glu Phe
        450                 455                 460

Glu Ala Met Asp Thr Leu
465                 470

<210> SEQ ID NO 2
<211> LENGTH: 470
<212> TYPE: PRT
<213> ORGANISM: Artificial sequence
<220> FEATURE:
<223> OTHER INFORMATION: Synthetic peptide

<400> SEQUENCE: 2

Met Val Gln Ala Lys Ala Gly Phe Lys Ala Gly Val Gln Asp Tyr Arg
1               5                   10                  15

Leu Thr Tyr Tyr Thr Pro Asp Tyr Thr Pro Lys Asp Thr Asp Leu Leu
            20                  25                  30

Ala Cys Phe Arg Met Thr Pro Gln Pro Gly Val Pro Ala Glu Glu Ala
        35                  40                  45
```

-continued

```
Ala Ala Ala Val Ala Ala Glu Ser Ser Thr Gly Thr Trp Thr Thr Val
     50                  55                  60
Trp Thr Asp Asn Met Thr Asp Leu Asp Arg Tyr Lys Gly Arg Cys Tyr
 65                  70                  75                  80
Asp Met Glu Ala Val Pro Asn Glu Asp Asn Gln Tyr Phe Ala Phe Met
                 85                  90                  95
Ala Tyr Pro Leu Asp Met Phe Glu Glu Gly Ser Val Thr Asn Val Leu
             100                 105                 110
Thr Ser Leu Val Gly Asn Val Phe Gly Phe Lys Ala Leu Arg Ala Leu
             115                 120                 125
Arg Leu Glu Asp Met Arg Phe Pro Val Ala Leu Ile Lys Thr Phe Gln
 130                 135                 140
Gly Pro Pro His Gly Ile Thr Val Glu Arg Asp Lys Leu Asn Lys Tyr
 145                 150                 155                 160
Gly Arg Pro Leu Leu Gly Cys Thr Ile Lys Pro Lys Leu Gly Leu Ser
                 165                 170                 175
Ala Lys Asn Tyr Gly Arg Ala Val Tyr Glu Cys Leu Arg Gly Gly Leu
             180                 185                 190
Asp Phe Thr Lys Asp Asp Glu Asn Ile Asn Ser Gln Pro Phe Met Arg
             195                 200                 205
Trp Arg Asp Arg Phe Met Phe Val Gln Glu Ala Ile Glu Lys Ala Gln
 210                 215                 220
Ala Glu Thr Asn Glu Met Lys Gly His Tyr Leu Asn Val Thr Ala Gly
 225                 230                 235                 240
Thr Cys Glu Glu Met Met Lys Arg Ala Glu Phe Ala Lys Glu Met Gly
                 245                 250                 255
Thr Pro Ile Ile Met His Asp Phe Phe Thr Gly Gly Phe Thr Ala Asn
             260                 265                 270
Thr Thr Leu Ala Arg Trp Cys Arg Asp Asn Gly Ile Leu Leu His Ile
 275                 280                 285
His Arg Ala Met His Ala Val Val Asp Arg Gln Lys Asn His Gly Met
 290                 295                 300
His Phe Arg Val Leu Ala Lys Cys Leu Arg Leu Ser Gly Gly Asp His
 305                 310                 315                 320
Leu His Ser Gly Thr Val Val Gly Lys Leu Glu Gly Glu Arg Gly Met
                 325                 330                 335
Thr Met Gly Phe Val Asp Leu Met Arg Glu Asp Tyr Val Glu Glu Asp
             340                 345                 350
Arg Ser Arg Gly Met Phe Phe Thr Gln Asp Tyr Ala Ser Met Pro Gly
             355                 360                 365
Thr Met Pro Val Ala Ser Gly Gly Ile His Val Trp His Met Pro Ala
 370                 375                 380
Leu Val Glu Met Phe Gly Asp Asp Ser Cys Leu Gln Phe Gly Gly Gly
 385                 390                 395                 400
Thr Met Gly His Pro Trp Gly Asn Ala Pro Gly Ala Thr Ala Asn Arg
                 405                 410                 415
Val Ala Leu Glu Ala Cys Val Gln Ala Arg Asn Glu Gly Arg Asn Leu
             420                 425                 430
Ala Arg Glu Gly Asn Asp Val Ile Arg Glu Ala Cys Arg Trp Ser Pro
             435                 440                 445
```

```
Glu Leu Ala Ala Ala Cys Glu Leu Trp Lys Glu Met Lys Phe Glu Phe
    450                 455                 460
Glu Ala Met Asp Thr Met
465                 470

<210> SEQ ID NO 3
<211> LENGTH: 470
<212> TYPE: PRT
<213> ORGANISM: Artificial sequence
<220> FEATURE:
<223> OTHER INFORMATION: Synthetic peptide

<400> SEQUENCE: 3

Met Val Gln Ala Lys Ala Gly Phe Lys Ala Gly Val Gln Asp Tyr Arg
1               5                   10                  15

Leu Thr Tyr Tyr Thr Pro Asp Tyr Thr Pro Lys Asp Thr Asp Leu Leu
            20                  25                  30

Ala Cys Phe Arg Met Thr Pro Gln Pro Gly Val Pro Ala Glu Glu Ala
        35                  40                  45

Ala Ala Val Ala Ala Glu Ser Ser Thr Gly Thr Trp Thr Thr Val
    50                  55                  60

Trp Thr Asp Asn Met Thr Asp Leu Asp Arg Tyr Lys Gly Arg Cys Tyr
65                  70                  75                  80

Asp Met Glu Ala Val Pro Asn Glu Asp Asn Gln Tyr Phe Ala Phe Met
                85                  90                  95

Ala Tyr Pro Leu Asp Met Phe Glu Glu Gly Ser Val Thr Asn Val Leu
            100                 105                 110

Thr Ser Leu Val Gly Asn Val Phe Gly Phe Lys Ala Leu Arg Ala Leu
        115                 120                 125

Arg Leu Glu Asp Met Arg Phe Pro Val Ala Leu Ile Lys Thr Phe Gln
130                 135                 140

Gly Pro Pro His Gly Ile Thr Val Glu Arg Asp Lys Leu Asn Lys Tyr
145                 150                 155                 160

Gly Arg Pro Leu Leu Gly Cys Thr Ile Lys Pro Lys Leu Gly Leu Ser
                165                 170                 175

Ala Lys Asn Tyr Gly Arg Ala Val Tyr Glu Cys Leu Arg Gly Gly Leu
            180                 185                 190

Asp Phe Thr Lys Asp Asp Glu Asn Ile Asn Ser Gln Pro Phe Met Arg
        195                 200                 205

Trp Arg Asp Arg Phe Met Phe Val Gln Glu Ala Ile Glu Lys Ala Gln
210                 215                 220

Ala Glu Thr Asn Glu Met Lys Gly His Tyr Leu Asn Val Thr Ala Gly
225                 230                 235                 240

Thr Cys Glu Glu Met Met Lys Arg Ala Glu Phe Ala Lys Glu Met Gly
                245                 250                 255

Thr Pro Ile Ile Met His Asp Phe Phe Thr Gly Gly Phe Thr Ala Asn
            260                 265                 270

Thr Thr Leu Ala Arg Trp Cys Arg Asp Asn Gly Ile Leu Leu His Ile
        275                 280                 285

His Arg Ala Met His Ala Val Asp Arg Gln Lys Asn His Gly Met
290                 295                 300

His Phe Arg Val Leu Ala Lys Cys Leu Arg Leu Ser Gly Gly Asp His
305                 310                 315                 320

Leu His Ser Gly Thr Val Val Gly Lys Leu Glu Gly Glu Arg Gly Met
                325                 330                 335
```

```
Thr Met Gly Phe Val Asp Leu Met Arg Glu Asp Tyr Val Glu Glu Asp
            340                 345                 350

Arg Ser Arg Gly Met Phe Phe Thr Gln Asp Tyr Ala Ser Met Pro Gly
        355                 360                 365

Thr Met Pro Val Ala Ser Gly Gly Ile His Val Trp His Met Pro Ala
370                 375                 380

Leu Val Glu Met Phe Gly Asp Asp Ser Cys Leu Gln Phe Gly Gly Gly
385                 390                 395                 400

Thr Met Gly His Pro Trp Gly Asn Ala Pro Gly Ala Thr Ala Asn Arg
            405                 410                 415

Val Ala Leu Glu Ala Cys Val Gln Ala Arg Asn Glu Gly Arg Asn Leu
            420                 425                 430

Ala Arg Glu Gly Asn Asp Val Ile Arg Glu Ala Cys Arg Trp Ser Pro
        435                 440                 445

Glu Leu Ala Ala Ala Cys Glu Leu Trp Lys Glu Met Lys Phe Glu Phe
450                 455                 460

Glu Ala Met Asp Thr Met
465                 470

<210> SEQ ID NO 4
<211> LENGTH: 470
<212> TYPE: PRT
<213> ORGANISM: Artificial sequence
<220> FEATURE:
<223> OTHER INFORMATION: Synthetic peptide

<400> SEQUENCE: 4

Met Val Lys Ala Lys Ala Gly Phe Lys Ala Gly Val Lys Asp Tyr Lys
1               5                   10                  15

Leu Thr Tyr Tyr Thr Pro Asp Tyr Thr Pro Lys Asp Thr Asp Leu Leu
            20                  25                  30

Ala Cys Phe Lys Met Thr Pro Lys Pro Gly Val Pro Ala Glu Glu Ala
        35                  40                  45

Ala Ala Ala Val Ala Ala Lys Ser Ser Thr Gly Thr Trp Thr Thr Val
    50                  55                  60

Trp Thr Asp Asn Leu Thr Asp Leu Asp Lys Tyr Lys Gly Lys Cys Tyr
65                  70                  75                  80

Asp Leu Glu Ala Val Pro Asn Glu Asp Asn Lys Tyr Phe Ala Phe Ile
                85                  90                  95

Ala Tyr Pro Leu Asp Leu Phe Glu Lys Gly Ser Val Thr Asn Val Leu
            100                 105                 110

Thr Ser Leu Val Gly Asn Val Phe Gly Phe Lys Ala Leu Arg Ala Leu
        115                 120                 125

Arg Leu Glu Asp Ile Arg Phe Pro Val Ala Leu Ile Lys Thr Phe Gln
    130                 135                 140

Gly Pro Pro His Gly Ile Thr Val Glu Arg Asp Lys Leu Asn Lys Tyr
145                 150                 155                 160

Gly Arg Pro Leu Leu Gly Cys Thr Ile Lys Pro Lys Leu Gly Leu Ser
                165                 170                 175

Ala Lys Asn Tyr Gly Arg Ala Val Tyr Glu Cys Leu Arg Gly Gly Leu
            180                 185                 190

Asp Phe Thr Lys Asp Asp Glu Asn Ile Asn Ser Gln Pro Phe Met Arg
        195                 200                 205

Trp Arg Asp Arg Phe Leu Phe Val Gln Glu Ala Ile Glu Lys Ala Gln
    210                 215                 220
```

```
Ala Glu Thr Asn Glu Met Lys Gly His Tyr Leu Asn Val Thr Ala Gly
225                 230                 235                 240

Thr Cys Glu Glu Met Met Lys Arg Ala Glu Phe Ala Lys Glu Ile Gly
                245                 250                 255

Thr Pro Ile Ile Met His Asp Phe Phe Thr Gly Gly Phe Thr Ala Asn
            260                 265                 270

Thr Thr Leu Ala Arg Trp Cys Arg Asp Asn Gly Ile Leu Leu His Ile
        275                 280                 285

His Arg Ala Met His Ala Val Val Asp Arg Gln Lys Asn His Gly Ile
    290                 295                 300

His Phe Arg Val Leu Ala Lys Cys Leu Arg Leu Ser Gly Gly Asp His
305                 310                 315                 320

Leu His Ser Gly Thr Val Val Gly Lys Leu Glu Gly Glu Arg Gly Ile
                325                 330                 335

Thr Met Gly Phe Val Asp Leu Met Arg Glu Asp Tyr Val Glu Glu Asp
            340                 345                 350

Arg Ser Arg Gly Ile Phe Phe Thr Gln Asp Tyr Ala Ser Met Pro Gly
        355                 360                 365

Thr Met Pro Val Ala Ser Gly Gly Ile His Val Trp Lys Met Pro Ala
    370                 375                 380

Leu Val Glu Ile Phe Gly Asp Asp Ser Cys Leu Lys Phe Gly Gly Gly
385                 390                 395                 400

Thr Leu Gly Lys Pro Trp Gly Asn Ala Pro Gly Ala Thr Ala Asn Lys
                405                 410                 415

Val Ala Leu Glu Ala Cys Val Lys Ala Lys Asn Glu Gly Lys Asn Leu
            420                 425                 430

Ala Lys Glu Gly Asn Asp Val Ile Lys Glu Ala Cys Lys Trp Ser Pro
        435                 440                 445

Glu Leu Ala Ala Ala Cys Glu Leu Trp Lys Glu Ile Lys Phe Lys Phe
    450                 455                 460

Glu Ala Met Asp Thr Leu
465                 470

<210> SEQ ID NO 5
<211> LENGTH: 470
<212> TYPE: PRT
<213> ORGANISM: Artificial sequence
<220> FEATURE:
<223> OTHER INFORMATION: Synthetic peptide

<400> SEQUENCE: 5

Met Val Lys Ala Lys Ala Gly Phe Lys Ala Gly Val Gln Asp Tyr Lys
1               5                   10                  15

Leu Thr Tyr Tyr Thr Pro Asp Tyr Thr Pro Lys Asp Thr Asp Leu Leu
            20                  25                  30

Ala Cys Phe Lys Met Thr Pro Lys Pro Gly Val Pro Ala Glu Glu Ala
        35                  40                  45

Ala Ala Ala Val Ala Ala Glu Ser Ser Thr Gly Thr Trp Thr Thr Val
    50                  55                  60

Trp Thr Asp Asn Leu Thr Asp Leu Asp Lys Tyr Lys Gly Arg Cys Tyr
65                  70                  75                  80

Asp Leu Glu Ala Val Pro Asn Glu Asp Asn Lys Tyr Phe Ala Phe Ile
                85                  90                  95

Ala Tyr Pro Leu Asp Leu Phe Glu Glu Gly Ser Val Thr Asn Val Leu
            100                 105                 110
```

Thr Ser Leu Val Gly Asn Val Phe Gly Phe Lys Ala Leu Lys Ala Leu
    115                 120                 125

Arg Leu Glu Asp Ile Arg Phe Pro Val Ala Leu Ile Lys Thr Phe Gln
130                 135                 140

Gly Pro Pro His Gly Ile Thr Val Glu Arg Asp Lys Leu Asn Lys Tyr
145                 150                 155                 160

Gly Arg Pro Leu Leu Gly Cys Thr Ile Lys Pro Lys Leu Gly Leu Ser
                165                 170                 175

Ala Lys Asn Tyr Gly Arg Ala Val Tyr Glu Cys Leu Arg Gly Gly Leu
            180                 185                 190

Asp Phe Thr Lys Asp Asp Glu Asn Ile Asn Ser Gln Pro Phe Met Lys
            195                 200                 205

Trp Arg Asp Arg Phe Leu Phe Val Gln Glu Ala Ile Glu Lys Ala Gln
        210                 215                 220

Ala Glu Thr Asn Glu Met Lys Gly His Tyr Leu Asn Val Thr Ala Gly
225                 230                 235                 240

Thr Cys Glu Glu Met Met Lys Lys Ala Glu Phe Ala Lys Glu Ile Gly
                245                 250                 255

Thr Pro Ile Ile Met His Asp Phe Phe Thr Gly Gly Phe Thr Ala Asn
            260                 265                 270

Thr Thr Leu Ala Lys Trp Cys Arg Asp Asn Gly Ile Leu Leu His Ile
            275                 280                 285

His Arg Ala Met His Ala Val Val Asp Lys Gln Lys Asn His Gly Ile
        290                 295                 300

His Phe Arg Val Leu Ala Lys Cys Leu Arg Leu Ser Gly Gly Asp His
305                 310                 315                 320

Leu His Ser Gly Thr Val Val Gly Lys Leu Glu Gly Glu Arg Gly Ile
                325                 330                 335

Thr Met Gly Phe Val Asp Leu Met Lys Glu Asp Tyr Val Glu Glu Asp
            340                 345                 350

Arg Ser Arg Gly Ile Phe Phe Thr Gln Asp Tyr Ala Ser Met Pro Gly
            355                 360                 365

Thr Met Pro Val Ala Ser Gly Gly Ile His Val Trp Lys Met Pro Ala
        370                 375                 380

Leu Val Glu Ile Phe Gly Asp Asp Ser Cys Leu Lys Phe Gly Gly Gly
385                 390                 395                 400

Thr Leu Gly Lys Pro Trp Gly Asn Ala Pro Gly Ala Thr Ala Asn Lys
                405                 410                 415

Val Ala Leu Glu Ala Cys Val Gln Ala Lys Asn Glu Gly Lys Asn Leu
            420                 425                 430

Ala Lys Glu Gly Asn Asp Val Ile Lys Glu Ala Cys Lys Trp Ser Pro
            435                 440                 445

Glu Leu Ala Ala Ala Cys Glu Leu Trp Lys Glu Ile Lys Phe Glu Phe
        450                 455                 460

Glu Ala Met Asp Thr Leu
465                 470

ENGINEERING RUBISCO FOR FOOD SAFETY

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SD15512_ST25_2.txt," created on Oct. 12, 2020 (size of 21 kilobytes), which is hereby incorporated by reference in its entirety.

FIELD

This disclosure relates to genetic engineering of RuBisCo (Ribulose-1,5-bisphosphate carboxylase/oxygenase) from algal biomass.

BACKGROUND

Global demand for high quality digestible protein is expected to substantially outpace population growth over the coming decades, necessitating gains in feed-to-food conversion efficiency for sustainable food security. Toward these ends, identifying and producing new high quality protein feedstocks that supplement existing agriculture will be of major importance and have significant impacts that intersect with the energy and water infrastructure.

RuBisCo is the most abundant soluble protein on Earth, comprising in some cases over half of the protein content of green plant tissue and algae biomass. RuBisCo is already considered a nearly complete protein source based on substantial quantities of the essential amino acids for human nutrition (protein score=98/100 PDCAAS), yet further improvement could provide a complete and renewable food supply.

The FDA lists nine essential amino acids for human nutrition, with lysine (Lys or K) and methionine (Met or M) considered to be the first limiting; recommended daily allowances (RDA) of 31 and 21 mg/g of total protein, respectively. For non-ruminant and aquaculture applications, proteinaceous feed ingredient prices have increased between 67-284% over the last 15 years, and supplementation of Met and Lys is commonly the dominant cost of feed, approximated to be in excess of $2000/ton at modest purities (Rana and Hanson FAO 2009).

The current state of the art for supplementation of these amino acids in feeds is to utilize a processed animal source (e.g., menhaden fish), thereby negatively impacting the sustainability of increased commercial food production, especially aquaculture, the fastest growing food production method globally, as well as for non-ruminant farm animals. Since RuBisCo's biochemical function is to initiate fixation of $CO_2$, significant efforts have been made to engineer the protein, particularly for enhanced $CO_2/O_2$ selectivity. While basic discoveries in the modification and expression of genes in RuBisCo have been made (especially the large subunit of the RuBisCo complex, RbcL), despite much research on this project and funding, very limited success at accomplishing improvement in RuBisCo's CO fixation has been made.

SUMMARY

The amino acid sequences of the proteins in the RuBisCo complex indicate that it should be possible to utilize RuBisCo as a complete protein source for human (and non-ruminate) nutrition if the quantity of the first limiting amino acids, Methionine (Met) and Lysine (Lys), were doubled. This was achieved by generation of genetic constructs for expression of RbcL, the large subunit of RuBisCo, with codon swaps to increase the relative abundance of each of the target amino acids. This was a genome-integrated, stable expression of the Met- and Lys-enriched RbcL constructs. Analysis of the whole algae protein hydrolysates from the control and RbcL mutants indicated significantly improved amino acid score in the mutants, as well as enrichment of Met and Lys.

In an embodiment disclosed herein, a biological material comprises an amino acid sequence having at least 84% sequence identity to any one of SEQ ID Nos. 2-5 or an analog thereof.

In an embodiment, a food source includes a ribulose-1,5-bisphosphate carboxylase/oxygenase with an RbcL unit having an amino acid sequence with at least 84% sequence identity to any one of SEQ ID Nos. 2-5 or an analog thereof.

In an embodiment disclosed herein, a method of improving a ribulose-1,5-bisphosphate carboxylase/oxygenase (RuBisCo), includes the steps of: making a modified RbcL of the RuBisCo, by, on an RbcL unit of the RuBisCo: substituting Met for Leu, Phe, Val, or Ile or combinations thereof, substituting Lys for Arg, Thr, or His or combinations thereof, or both substituting Met for Leu, Phe, Val, or Ile or combinations thereof and substituting Lys for Arg, Thr, or His or combinations thereof. Then a modified RuBisCo with the modified RbcL is added to a biomass host.

DETAILED DESCRIPTION

Figure 1:
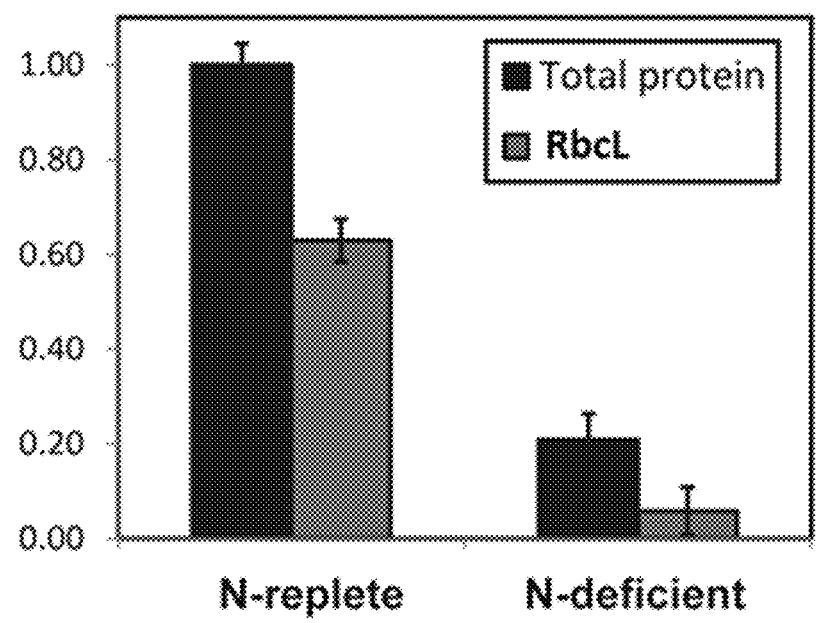
FIG. 1 is graph showing RuBisCo protein content in N-replate and N-deficient environments.

As used herein, the term "about" means+/−10% of any recited value. As used herein, this term modifies any recited value, range of values, or endpoints of one or more ranges.

The term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something, and is not intended to indicate a preference.

By "micro" is meant having at least one dimension that is less than 1 mm but equal to or larger than 1 µm. For instance, a microstructure (e.g., any structure described herein, such as a microparticle) can have a length, width, height, cross-sectional dimension, circumference, radius (e.g., external or internal radius), or diameter that is less than 1 mm but equal to or larger than 1 µm. In another instance, the microstructure has a dimension that is of from about 1 µm to 1 mm.

By "nano" is meant having at least one dimension that is less than 1 µm but equal to or larger than 1 nm. For instance, a nanostructure (e.g., any structure described herein, such as a nanoparticle) can have a length, width, height, cross-sectional dimension, circumference, radius (e.g., external or internal radius), or diameter that is less than 1 µm but equal to or larger than 1 nm. In another instance, the nanostructure has a dimension that is of from about 1 nm to about 1 µm.

The term "analog" as used herein referring to a protein or peptide means a modified protein or peptide wherein one or more amino acid residues of the peptide have been substituted by other amino acid residues, and/or wherein one or more amino acid residues have been deleted from the protein or peptide, and/or wherein one or more amino acid residues have been added to the protein or peptide. Such addition or deletion of amino acid residues can take place at the N-terminal of the peptide and/or at the C-terminal of the peptide.

The term "biological material" is used to refer to a biomass, a bacteria, a fungi, a peptide, a protein, a cell, DNA, RNA, a plastid, an amino acid sequence, or other biological compound that includes amino acids. A biological material can include other biological materials in it. For example, a biomass can include a cell, and cell can include a plastid, and a plastid can include various amino acid sequences. RuBisCo is biological material, and can include RbcL, a protein and a biological material.

The term "reporter" is used to describe an imaging agent or moiety that is incorporated into the outer layer or cargo of particles according to an embodiment of the present disclosure and provides a signal that can be measured. The moiety may provide a fluorescent signal or may be a radioisotope which allows radiation detection, among others. Exemplary fluorescent labels for use in particles (e.g., via conjugation or adsorption to the outer layer or the core, via integration into the matrix of the core, and/or via incorporation into cargo elements such as DNA, RNA-sn-glycero-3-phosphoethanolamine (Texas Red® DHPE, 583/608), Alexa Fluor® 647 hydrazide (649/666), Alexa Fluor® 647 carboxylic acid, succinimidyl ester (650/668), Ulysis™ Alexa Fluor® 647 Nucleic Acid Labeling Kit (650/670), Alexa Fluor® 647 conjugate of annexin V (650/665), other fluorescent labels, colorimetric labels, quantum dots, nanoparticles, microparticles, barcodes, radio labels (e.g., RF labels or barcodes), avidin, biotin, tags, dyes, an enzyme that can optionally include one or more linking agents and/or one or more dyes, as well as combinations thereof etc. Additional reporters can include a detection agent (e.g., a dye, such as an electroactive detection agent, a fluorescent dye, a luminescent dye, a chemiluminescent dye, a colorimetric dye, a radioactive agent, a contrast agent, etc.), a particle (e.g., such as a microparticle, a nanoparticle, a latex bead, a colloidal particle, a magnetic particle, a fluorescent particle, etc.), and/or a label (e.g., an electroactive label, an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes). Moieties that enhance the fluorescent signal or slow the fluorescent fading may also be incorporated and include SlowFade® Gold antifade reagent (with and without DAPI) and Image-iT® FX signal enhancer. All of these are well known in the art.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the disclosure. In certain embodiments, a polypeptide to be utilized in accordance with the disclosure includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the disclosure.

As used herein, when a peptide, polypeptide, protein. or nucleic acid sequence is referred to as having "at least X % sequence identity" to a reference sequence, it is meant that at least X percent of the amino acids or nucleotides in the peptide, polypeptide, protein, or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for peptides, the length of comparison sequences can be at least five amino acids, preferably 10, 20, 30, 40, up to the entire length of the peptide or protein. In general, for polypeptides, the length of comparison sequences can be at least five amino acids, such as, for example, 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

"Heterologous," as used herein, means a nucleotide or polypeptide sequence that is not found in the native nucleic acid or protein, respectively. A heterologous nucleic acid sequence may be linked to a naturally-occurring nucleic acid sequence (or a variant thereof) (e.g., by genetic engineering) to generate a chimeric nucleotide sequence encoding a chimeric polypeptide.

"Recombinant," as used herein, means that a particular nucleic acid, as defined herein, is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions and may indeed act to modulate production of a desired product by various mechanisms. Alternatively, DNA sequences encoding RNA (e.g., DNA-targeting RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention but may be a naturally occurring amino acid sequence.

By "cleavage" it is meant the breakage of the covalent backbone of a target sequence (e.g., a nucleic acid molecule). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guiding component and a nuclease is used for targeted double-stranded DNA cleavage. In other embodiments, a complex comprising a guiding component and a nuclease is used for targeted single-stranded RNA cleavage.

By "cleavage domain" or "active domain" or "nuclease domain" of a nuclease it is meant the amino acid sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

By an "effective amount" or a "sufficient amount" of an agent (e.g., a cargo), as used herein, is that amount sufficient to effect beneficial or desired results, such as clinical results, and, as such, an "effective amount" depends upon the context in which it is being applied. For example, in the context of administering an agent that employs a CRISPR component to genetically modify a gene, an effective amount of an agent is, for example, an amount sufficient to achieve increased or decreased expression of that gene, as compared to the response obtained without administration of the agent.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof. A substitution as used herein requires an attachment.

Disclosed herein are technologies to improve the essential amino acid profile of RuBisCo. Using such modified RuBisCo for improving for human, terrestrial, and mariculture feeds would valorize the most abundant and underutilized soluble biomass-derived protein source, and provide a scalable technology basis for eliminating global protein deficiency. In addition to its abundance, RuBisCo is easy to extract and highly digestible, as well as having other favorable chemical and mechanical properties for feed applications, including foam formation and gelation. Although RuBisCo is already considered a nearly complete protein source based on substantial quantities of the essential amino acids for human nutrition (protein score=98/100), significant improvements are possible by increasing incorporation of two key amino acids, methionine (Met) and lysine (Lys), which are typically limiting and costly for a variety feed applications.

As disclosed herein, improvement of RuBisCo was accomplished by generation of genetic constructs for expression of RbcL, the large subunit of RuBisCo, with strategically positioned codon swaps to increase the relative abundance of each of the target amino acids, based on Graham's distance matrix proximity and non-disruption of enzyme structure or function. Rbcl is encoded by chloroplasts in plants such as algae or other plants in leafy biomass. Then, genome integrated, stable expression of the Met- and Lys-enriched RbcL constructs was demonstrated. Finally, analysis of the amino acid profiles from whole algae protein hydrolysates from the control and Met- and Lys-enriched RbcL mutants were conducted and indicated significantly improved amino acid score in the mutants, as well as enrichment of Met and Lys. These results provide a technological basis for addressing scaling and sustainability issues associated with rapidly growing global protein demand.

RuBisCo

RuBisCo is a complex of eight catalytic large subunit (RbcL) and eight regulatory small subunits (RbcS). RbcS may have a sequence length of 165 to 180 units, such as 166 to 178 units, or 170 to 175 units, and RbcL may have a sequence length of 440 to 475 units, such as 445 to 470, or 450 to 465 units. The weight-average molecular weight (Mw) may be 12,000 to 55,000 Da. RbcS has an Mw of 12,000 to 15,000 Da and RbcL has an Mw of 52,000 to 55,000 Da, such as 52,500 to 54,500 Da, or 53,000 to 54,000 Da. RuBisCo catalyzes two reactions in plant biomass, the carboxylation of D-ribulose 1,5-bisphosphate, which is the primary event in carbon dioxide fixation; and the oxidative fragmentation of the pentose substrate in the photorespiration process. Both reactions occur simultaneously and in competition at the same active site. If the mutations cause a disruption in either of these functions, then the system will not only lose its functionality but will also die off because these functions are also central to RuBisCo's Sources of biomass used as a starting material for the process disclosed herein include herbaceous or woody crops; crop residues, such as stalks and leaves of agricultural crops; forestry residues, such as unmerchantable timber remnants; and algal or cyanobacterial feedstocks. The biomass source (or at least RuBisCo portion) should be amenable to solubilization and hydrolysis of biopolymers contained therein. RuBisCo makes up the major fraction of easily soluble, hydrolysable, and mechanically processed protein. The remaining proteins are largely structure, and more recalcitrant to processing in general.

The experiments disclosed herein were conducted in a cyanobacterial and algae species, *Neochloris oleoabundans* and *Synechocystis*, or *E. coli*. *Synechocystis* is a genus of unicellular, freshwater cyanobacteria in the family Merismopediaceae. *Synechocystis* is a photosynthetic cyanobacteria and is representative of the simplest photosynthetic host for genetic manipulation; genetic modification for this host can be extended to many other green algae or green leafy biomass hosts. Other Cyanobacterias that can be used include other fast growing cyanos such as species 2973 and 11901. *Neochloris* is a lipidic microalga belonging in the class Chlorophyceae.

*E. coli* is a model bacterial host for enzymology. *E. coli* was used in this study to verify protein expression in a reduced system, absent photosynthetic apparati, to verify that the cyanobacteria process worked as expected. While *E. Coli* was used in the process disclosed herein to improve RuBisCo, this and related (*Corynebacterium glutamicum*) could be used for RuBisCo production in heterotrophic fermentation, as opposed to photoautotrophically.

In *Neochloris oleoabundans*, a preliminary analysis was made to determine the role of autophagy in regulation of RuBisCo expression or degradation based on nutrient stress-based lipid upregulation. FIG. 1 shows that under nitrogen-replete conditions, RuBisCo accounts for >60% of the total protein in the biomass (based on RbcL equivalents in the RuBisCo complex). Under N-deficiency the total protein is reduced by >75% with RuBisCo being disproportionately degraded, indicating that nutrient replete conditions are required for efficient RbcL production, especially with additional Met and Lys incorporation, since these are enriched with sulfur and nitrogen, respectively.

Figure 2:
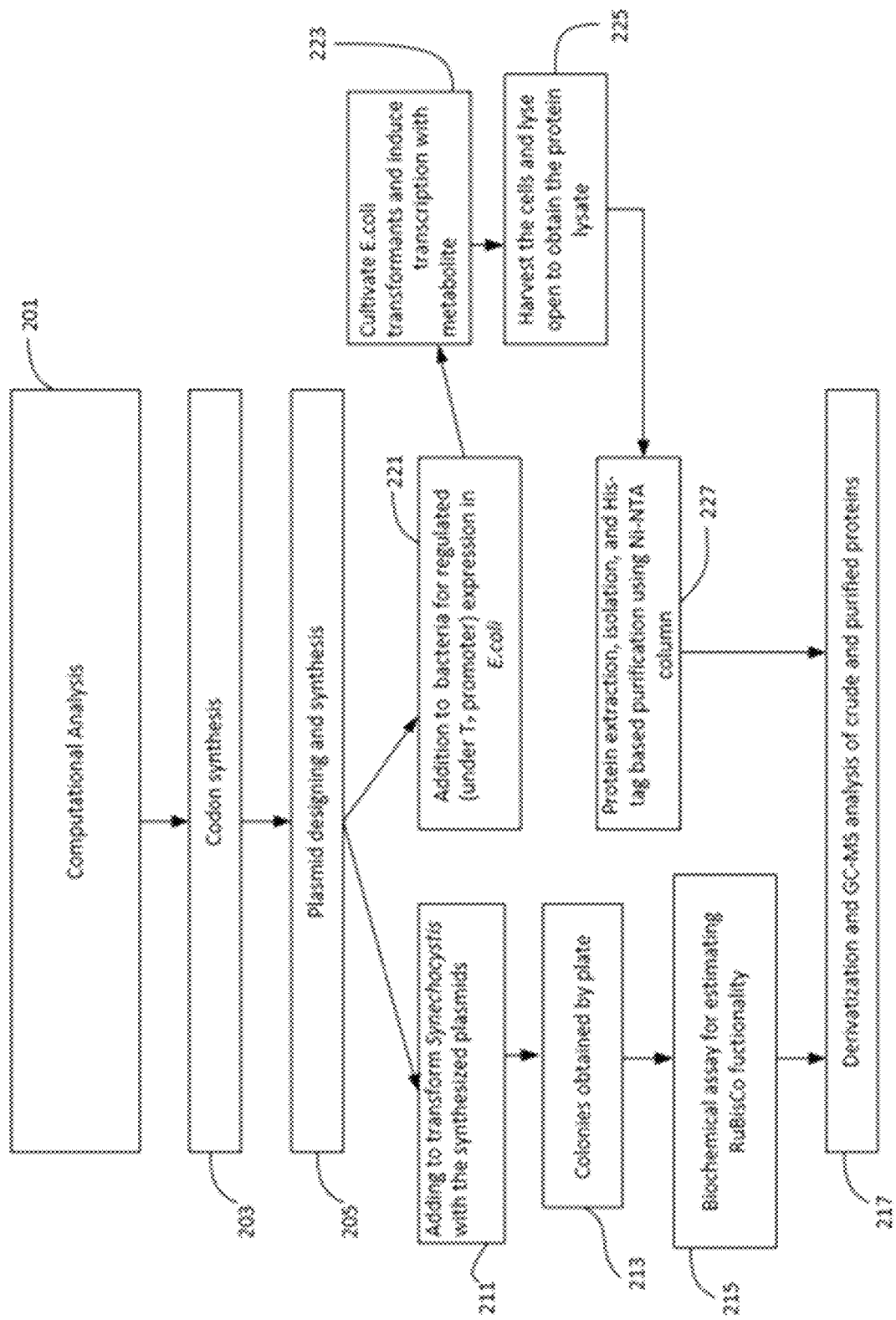
FIG. 2 is a flow chart showing a method of designing and synthesizing a fully functional RuBisCo variant with enhanced amino acid profile for food and feed applications.

Referring to FIG. 2, the strategy for achieving a fully functional RuBisCo variant with enhanced amino acid profile for food and feed applications starts with a tiered computational analysis and synthesis and design steps 201-205. This includes scanning for Lys and Met mutagenesis on the Rbcl unit of RuBisCo. These steps are for the goal of designing a precise amino acid replacement strategy to improve the Met and/or Lys content while keeping the RuBisCo functionality unaltered or improved after the mutagenesis. If the primary functionality for carbon fixation is destroyed through the mutation, then the algal biomass will die and the process will cease. Prior work to modify RuBisCo for improved carbon fixation has been difficult and met with many failures upon mutation.

In the computational analysis step 201, a computer-assisted RuBisCo sequence design and analysis is performed. Input to the computerized process is known sequences of RuBisCo and modification is based on utilization of Grantham's distance matrix. Through Grantham's distance matrix concomitant amino acid units that have a greater likelihood of being replaceable can be identified in the RuBisCo sequence based on their similarities to Met and Lys.

Grantham's distance matrix depicts distances between the amino acids on the basis of their structural and functional characteristics and was generated to study protein evolution. The matrix predicts that, compared to other amino acids; Arg, Thr and His are nearer to Lys while Leu, Phe, Val, Ile are closer to Met in terms of their substitution propensities. This indicates that replacement of these amino acids by Lys and Met, respectively, might not affect the protein folding and thus might not affect the functionality.

The methodology disclosed herein focused on mutations to the major subunit of the native *Synechocystis* RuBisCo, Rbcl. This Rbcl has 14 Met and 20 Lys residues. Based on Grantham's distance matrix there are 106 sites (marked in bold in FIG. 3 and excluding Met) that could be replaced by codons for methionine. Likewise, there are 55 sites (marked in underlining in FIG. 1 and excluding Lys) that could be replaced by codons for lysine.

In an embodiment, 1 to 30 Met residues, such as 14 to 25, or 15 to 20 can be substituted to the Rbcl subunit at various locations in the 106 identified Leu, Phe, Val, and Ile substitutions sites. In an embodiment, 1 to 40 Lys residues, such as 4 to 35, or 20 to 30 can be substituted into the Rbcl subunit at various locations in the 55 identified Arg, Thr, and His substitutions sites.

As a second design consideration, certain amino acids constitute essential functionality in the Rbcl protein, and these positions should be kept unchanged. Uniprot annotations can be reviewed to assist in this process.

In a third design consideration, a further restriction of mutation locations can be calculated based on enzyme activity concerns, e.g. relative distance to protein-protein and protein-substrate binding domains, and translation initiating and terminating codons based on standard plasmid design principles.

After the RbcL mutations are planned and designed through the computational analysis step 201, codons for assembling the modified RbcL are synthesized at 203. This may also involve computer aided analysis based on known codons for the amino acid sequences of the modified RbcL in the desired biomass medium, e.g. cyanobacteria, algae, or *E. Coli*.

A plasmid is an extrachromosomal circular DNA that, in this case, replicates independently in the biomass host. Plasmids can be found in bacteria, archaea and eukaryotes. At plasmid designing and synthesis step 205 a plasmid is designed and constructed for assembling the modified RbcL determined from computational analysis step 201.

Figure 3:
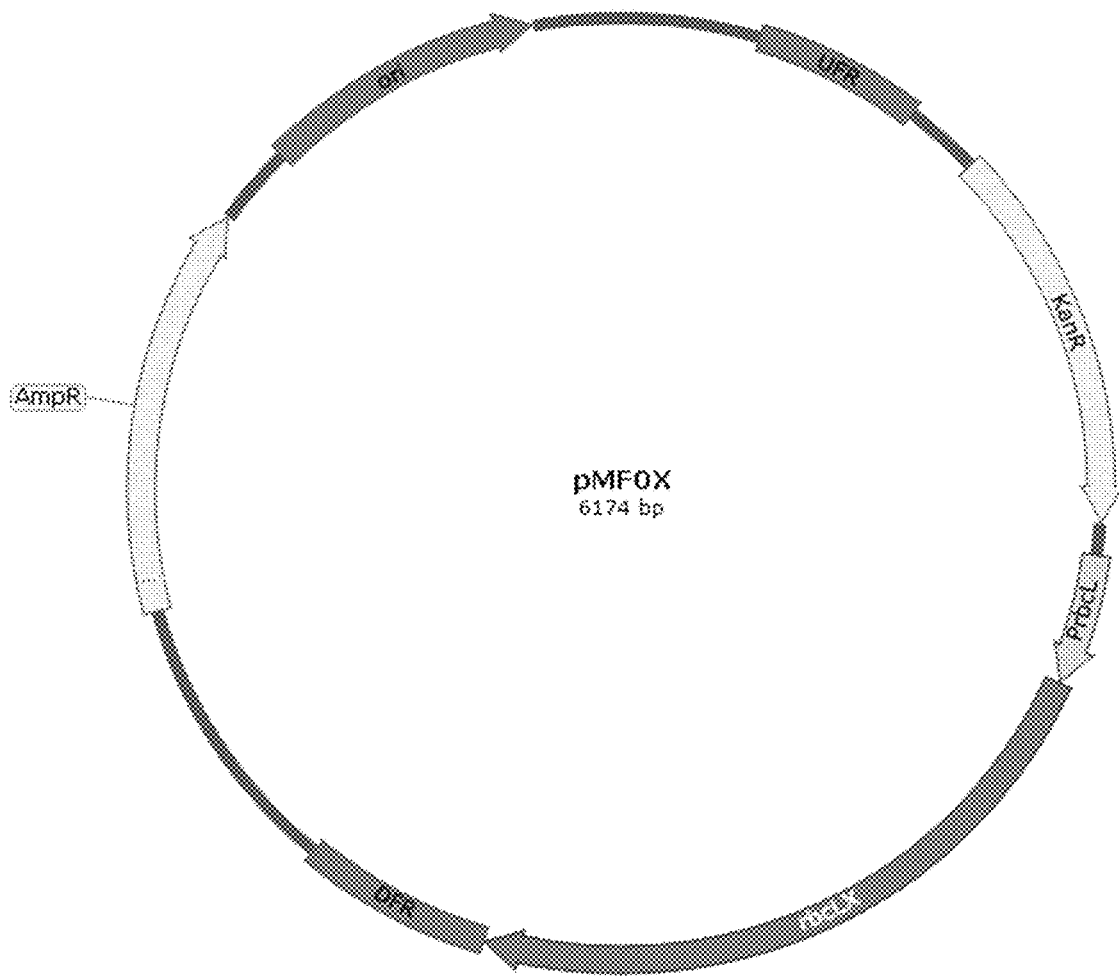
FIG. 3 is an example plasmid map.

An example plasmid map is shown in FIG. 3. Here a recombinant plasmid construct is shown designed for the expression of variant RbcL genes in *Synechocystis* 6803. The construct may been designed to replace the native RbcL gene along with its promoter with the native Rbcl promoter and the variant RbcL genes. This is a general plasmid map, where X can be 1, 2, 3 etc., based on the number of variant genes designed for expression. The upstream flanking region (UFR) and downstream flanking region (DFR) may be designed to integrate the construct into a specific loci in the genomic DNA of host strain through homologous recombination.

In the example method of FIG. 2 plasmids are designed and made for cyanobacteria and bacteria hosts. The codons from codon synthesis step 203 are used to construct the plasmids that will express the modified RbcL of RuBisCo.

In an embodiment, the RbcL in *Synechocystis* has a sequence corresponding to

SEQ ID No. 1:
MVQAKAGFKAGVQDYRLTYYTPDYTPKDTDLLACFRMTPQPGVPAEEAAA

AVAAESSTGTWTTVWTDNLTDLDRYKGRCYDLEAVPNEDNQYFAFIAYPL

-continued
DLFEEGSVTNVL<u>TS</u>LVGNVFGFKALRALRLEDIRFPVALIKTFQGPPHGI

TVERDKLNKYGRPLLGCTIKPKLGLSAKNYGRAVYECLRGGLDFTKDDEN

INSQPFMRWRDRFLFVQEAIEKAQAETNEMKGHYLNVTAGTCEEMMKRAE

FAKEIGTPIIMHDFFTGGFTANTTLARWCRDNGILLHIHRAMHAVVDRQK

NHGIHFRVLAKCLRLSGGDHLHSGTVVGKLEGERGITMGFVDLMREDYVE

EDRSRGIFFTQDYASMPGTMPVASGGIHVW<u>HMPALVEIFGDDSCLQFGGG</u>

<u>TLGHPWGNAPGATANRVALEACVQARNEGRNLAREGNDVIREACRWSPEL</u>

<u>AAACELWKEIKFEFEAMDTL</u>.

In an embodiment, after applying the computational analysis step 201, in the underlined portions, Isoleucine (I) and Leucine (L) are replaced with methionine (M). In another embodiment, Arginine (R) and Histidine (H) are replaced with Lysine (K) in the non-underlined portion. In an embodiment, a total of 14 M replacement are made, and in another embodiment, a total of 21K replacements are made. In an embodiment, only the end portions are modified, excluding mutations in the region 111-381. In another embodiment, mutations were spread across the entire sequence.

The following SEQ ID Nos. 2-5, show modified RbcL units with replacements made after the computational analysis step. In Sequences 2 and 3 14 M replacements were made. In Sequences 4 and 5, 21 K replacement were made. The 3 numbers at the end of the sequence indicate GMQE, QSQE, and Identity score with reference to an Rbcl protein 3zxw.1.I from the Swissmodel database.

(RbcL 1 A)
Sequence No. 2
MVQAKAGFKAGVQDYRMTYYTPDYTPKDTDMLACFRMTPQPGVPAEEAAA

AMAAESSTGTWTTVWTDNMTDLDRYKGRCYDMEAVPNEDNQYFAFMAYPL

DMFEEGSVTNVLTSLVGNVFGFKALRALRLEDIRFPVALIKTFQGPPHGI

TVERDKLNKYGRPLLGCTIKPKLGLSAKNYGRAVYECLRGGLDFTKDDEN

INSQPFMRWRDRFLFVQEAIEKAQAETNEMKGHYLNVTAGTCEEMMKRAE

FAKEIGTPIIMHDFFTGGFTANTTLARWCRDNGILLHIHRAMHAVVDRQK

NHGIHFRVLAKCLRLSGGDHLHSGTVVGKLEGERGITMGFVDLMREDYVE

EDRSRGIFFTQDYASMPGTMPVASGGIHVWHMPALVEMFGDDSCLQFGGG

TMGHPWGNAPGATANRVAMEACVQARNEGRNLAREGNDVMREACRWSPEM

AAACELWKEMKFEFEAMDTM (99, 99, 82.83)

(RbcL 2 A)
Sequence ID No. 3
MVQAKAGFKAGVQDYRLTYYTPDYTPKDTDLLACFRMTPQPGVPAEEAAA

AVAAESSTGTWTTVWTDNMTDLDRYKGRCYDMEAVPNEDNQYFAFMAYPL

DMFEEGSVTNVLTSLVGNVFGFKALRALRLEDMRFPVALIKTFQGPPHGI

TVERDKLNKYGRPLLGCTIKPKLGLSAKNYGRAVYECLRGGLDFTKDDEN

INSQPFMRWRDRFMVQEAIEKAQAETNEMKGHYLNVTAGTCEEMMKRAE

FAKEMGTPIIMHDFFTGGFTANTTLARWCRDNGILLHIHRAMHAVVDRQK

NHGMHFRVLAKCLRLSGGDHLHSGTVVGKLEGERGMTMGFVDLMREDYVE

EDRSRGMFFTQDYASMPGTMPVASGGIHVWHMPALVEMFGDDSCLQFGGG

-continued

TMGHPWGNAPGATANRVALEACVQARNEGRNLAREGNDVIREACRWSPEL

AAACELWKEMKFEFEAMDTM (99, 98, 83.26)

(RbcL3)
Sequence ID No. 4
MVKAKAGFKAGVKDYKLTYYTPDYTPKDTDLLACFKMTPKPGVPAEEAAA

AVAAKSSTGTWTTVWTDNLTDLDKYKGKCYDLEAVPNEDNKYFAFIAYPL

DLFEKGSVTNVLTSLVGNVFGFKALRALRLEDIRFPVALIKTFQGPPHGI

TVERDKLNKYGRPLLGCTIKPKLGLSAKNYGRAVYECLRGGLDFTKDDEN

INSQPFMRWRDRFLFVQEAIEKAQAETNEMKGHYLNVTAGTCEEMMKRAE

FAKEIGTPIIMHDFFTGGFTANTTLARWCRDNGILLHIHRAMHAVVDRQK

NHGIHFRVLAKCLRLSGGDHLHSGTVVGKLEGERGITMGFVDLMREDYVE

EDRSRGIFFTQDYASMPGTMPVASGGIHVWKMPALVEIFGDDSCLKFGGG

TLGKPWGNAPGATANKVALEACVKAKNEGKNLAKEGNDVIKEACKWSPEL

AAACELWKEIKFKFEAMDTL (98, 99, 81.37)

(RbcL4)
Sequence ID No. 5
MVKAKAGFKAGVQDYKLTYYTPDYTPKDTDLLACFKMTPKPGVPAEEAAA

AVAAESSTGTWTTVWTDNLTDLDKYKGRCYDLEAVPNEDNKYFAFIAYPL

DLFEEGSVTNVLTSLVGNVFGFKALKALRLEDIRFPVALIKTFQGPPHGI

TVERDKLNKYGRPLLGCTIKPKLGLSAKNYGRAVYECLRGGLDFTKDDEN

INSQPFMKWRDRFLFVQEAIEKAQAETNEMKGHYLNVTAGTCEEMMKKAE

FAKEIGTPIIMHDFFTGGFTANTTLAKWCRDNGILLHIHRAMHAVVDKQK

NHGIHFRVLAKCLRLSGGDHLHSGTVVGKLEGERGITMGFVDLMKEDYVE

EDRSRGIFFTQDYASMPGTMPVASGGIHVWKMPALVEIFGDDSCLKFGGG

TLGKPWGNAPGATANKVALEACVQAKNEGKNLAKEGNDVIKEACKWSPEL

AAACELWKEIKFEFEAMDTL (98, 98, 81.76)

In an embodiment, the modified sequence of the RbcL can be selected from analogs thereof and those with at least 84% sequence identity to one or any of Sequence ID Nos. 2-5, based on the entire chain length, wherein X is 85%, 90%, 95%, or 99%. In an embodiment, only modified RbcL units that are artificially synthesized and do not occur in nature are covered by the modified RbcL units and their analogs disclosed herein. In an embodiment, analogs of the modified RbcL are not included.

At transformation step 211, a cyanobacteria host, for example, as shown herein, Synechocystis (species PCC 6803) is transformed by introducing the engineered plasmid from the plasmid designing and synthesis step 205. The engineered plasmid replicates in both nuclear DNA and plastid DNA of the host, expressing the modified RuBisCo with improved protein score. The culture produces a stable, genome-integrated mutant of RuBisCo.

At 213 colonies can be obtained on an agar plate for analysis. These colonies can be further assayed to determine the RuBisCo functionality and confirm the culture is stable, i.e., that it is homologous and recombinant. Growth is an indirect measure of RuBisCo functionality.

At 215 further assay steps are performed for assessing the modified RuBisCo functionality. This may include testing to determine if the modified RbcL or modified RuBisCo has attained homologous recombination and if nuclear and plasmid DNA insertion is occurring. The goal being to produce a stable, genome-integrated RuBisCo mutant.

At step 217 the mutated RuBisCo is derivatized and a GC-MS analysis is made of the crude and purified proteins. In this example the results can be compared with the modified RuBisCo from the algal (Synechocystis) and bacterial (E. coli) samples to determine if the final product is the same.

Another route for expression and cultivation of the example modified RbcL and RuBisCo is disclosed for a bacterial host. At step 221 a bacterial host, E. Coli (e.g. BL21-DE3), is transformed by introducing the engineered plasmid from plasmid designing and synthesis step 205. In an embodiment, a promoter may be used, such as, a T7 RNA polymerase promoter, to promote the expression in E. Coli.

At step 223 the E. Coli transformants are cultivated and transcription of the modified RBcL is induced with a metabolite such as isopropyl β-d-1-thiogalactopyranoside (IPTG).

At step 225 the cultivated E. Coli transformants are lysed and the E. Coli protein enriched with the modified RbcL lysate is obtained.

At step 227 the modified RbcL lysate is loaded onto a chromatography column, such as a Ni-NTA column, for purification extraction. The resin bound proteins are isolated by, for example, adding an imidazole using a basic buffer solution, e.g., 7.5 to 9, or 7.8 to 8.5 pH.

Step 217 can follow step 227 or step 21,5 and, as discussed above, the mutated RuBisCo is derivatized and a GC-MS analysis is made of the crude and purified RuBisCo proteins. Again, the results can be compared with the modified RuBisCo from the algal (Synechocystis) and bacterial (E. Coli) samples to determine if the final product is the same.

In an embodiment, the engineered plasmid replicates in both nuclear DNA and plastid DNA of the host, expressing the modified RuBisCo with an improved protein score. The culture produces a stable, genome-integrated mutant of RuBisCo.

Figure 4:
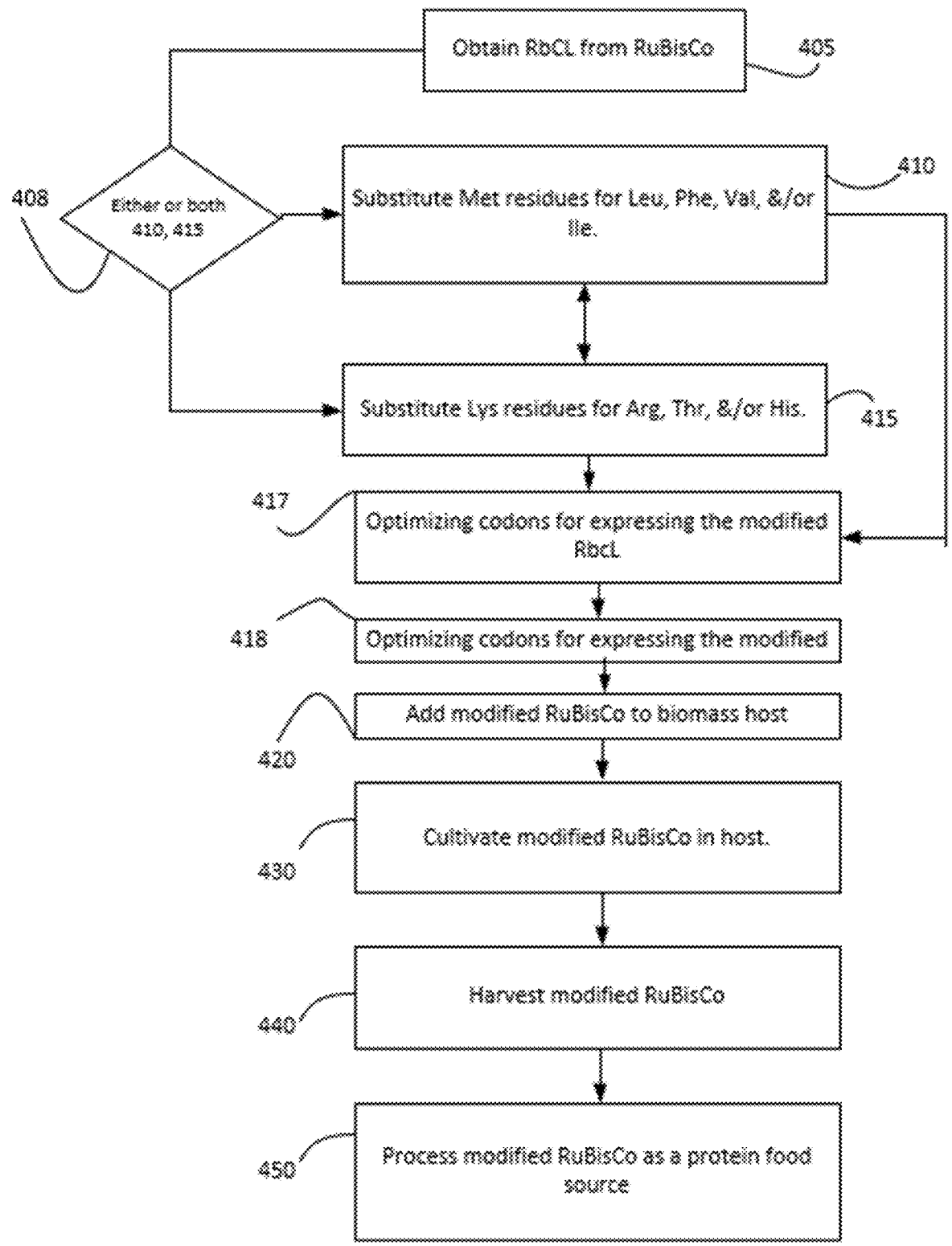
FIG. 4 example flow chart for making and using the modified RuBisCo.

In FIG. 4, an example process for making and using the modified RuBisCo is disclosed.

At step 405 a source of RuBisCo containing RbcL is identified and precipitated from solution using acid/base shift, with or without isolation of RbcL from RuBisCo complex.

At step 408 a decision is made as to whether either or both Met and/or Lys substitutions will be made on the RbcL. This will determine whether either Met substitution step 410 or Lys substitution step 415 are taken, or both. In embodiments where both steps are performed, Met substitution step 410 is performed first, then Lys substitution step 415 is performed; or Lys substitution step 415 is performed first and Met substitution step 410 is performed second. In an embodiment, they are performed simultaneously, i.e., in the same lab reaction.

At Met substitution step 410 Met is substituted on the source RbcL for Leu, Phe, Val, or Ile or combinations thereof. The location and number of substitutions may be driven by the results of the computational analysis step disclosed in FIG. 2. In an embodiment, only Met is substituted and 1 to 30 substitutions are made with the optional ranges as disclosed above. In an embodiment, only one of Leu, Phe, Val, and Ile in the source RbcL are substituted. In an embodiment, combinations of any of these are substituted.

At Lys substitution step 415 Lys is substituted on the source RbcL for Arg, Thr, or His or combinations thereof. The location and number of substitutions may be driven by the results of the computational analysis step disclosed in FIG. 2. In an embodiment, only Lys is substituted and 1 to 40 substitutions are made with the optional ranges as disclosed above. In an embodiment, only one of Arg, Thr, and His in the source RbcL are substituted. In an embodiment, combinations of any of these are substituted.

At step 417 codons are optimized for generating the modified RbcL

At step 418 a plasmid is constructed to replicate the modified RbcL with homologous recombination in a biomass host.

At step 420 the modified RuBisCo, i.e., the RbcL modified with the substitutions from Met substitution step 410 and/or Lys substitution step 415, is added to a biomass host, e.g., by introduction of the plasmid of step 418. The modified RbcL is stably incorporated into the RuBisCo complex. The biomass may be those disclosed herein, such as an algal cyanobacteria or *E. Coli*. The biomass may be cultivated in marine, brackish, or fresh water environments.

At step 430 the modified RuBisCo is cultivated in the host. This involves maintaining sufficient nutrients, such as nitrogen, and pH in the biomass, enabling the modified RuBisCo to replicate and grow as a stable, genome-integrated mutant species. The cultivation step, may take from 1 day to 12 months, such as 1 week to 6 month, or 1 month to 3 months, to grow a desirable quantity of the modified RuBisCo.

In an embodiment, sufficient pH levels, are, for example, 5.5 to 11.0, such as 6 to 9.5, 6.5 to 8.5. Coastal estuaries may be a particular advantageous location for such biomass growth and harvesting. It presents a brackish area of salt water, often with sufficient pH levels, with protection from mechanical disruption and dispersion from waves. Areas that have natural fertilizer run-off may present a convenient source of nitrogen to foster continued growth. Areas exposed to the sun are also desirable for the phot-respiration process.

At step 440, the modified RuBisCo is harvested after the period of cultivation. Harvesting may include pushing, sucking, or skimming the biomass from the environment, typically a body of water. Separation and enrichment of RuBisCo from the whole biomass via precipitation of the soluble proteins can then be performed under base shift conditions. See, e.g., Kobbi, S., Bougatef, A., Le flem, G. et al. Purification and Recovery of RuBisCO Protein from Alfalfa Green Juice: Antioxidative Properties of Generated Protein Hydrolysate. Waste Biomass Valor 8, 493-504 (2017) incorporated herein by reference.

Then at step 450, the modified RuBisCo can be processed further to make it a useful and preferably a palatable food source for different end uses. The modified RuBisCo can be used as a food source for many types of animals. It has a gelatinous, taste-less character, which could be flavored or mixed with other ingredients to make it more appealing. The enhanced RuBisCo could be particularly useful as an animal feed for animals that require a higher protein content, such as fish, or other marine animals, e.g., mussels, as well as chicken and swine. While ruminants do not require a high protein diet, the improved RuBisCo can also find use as a feedsource for ruminants.

In an embodiment, where the modified RuBisCo is used as a fish food it could be grown in the body of water with the fish it is intended to feed and no harvesting steps may be necessary.

In an embodiment, the modified RuBisCo has a PDCAAS protein score of greater than 98, such as, for example, 98.1 to 120, or 98.5 to 100, or 99 to 99.9. In an embodiment, the modified RuBisCo has a viscosity of 1 to 1,000 mPas at a shear rate of 100 (1/s), such as 10 to 500 mPas or 50 to 200 mPas.

EXAMPLES

Example 1

After performing computational analysis as described above in FIG. 2 and its accompanying text above, four mutant RbcLs were synthesized from an RbcL corresponding to SEQ ID No. 1. In particular, Graham's distance matrix was used to determine likely substitution locations for Met and Lys, then Uni-Prot annotations were deciphered to determine some substitutions that should be avoided to prevent lethal mutations. Finally, further computations based on enzymatic concerns (e.g., protein-protein and protein-substrate binding) were accounted for to determine four example mutant RbcL sequences.

Methionine replacements were conducted in pMF01 and pMF02, and these corresponded to SEQ ID Nos. 2 and 3. Lysine replacements were conducted in pMF03 and pMF04, and these corresponded to SEQ ID Nos. 4 and 5.

RuBisCO amino acid sequence of *Synechocystis* Sp. PCC 6803 was obtained from UniProt online database. The RuBisCO amino acid sequence was then modified by replacing the similar amino acid for methionine and lysine according to Grantham's distance difference D index to increase the number of Lysine and Methionine by approximately two-fold.

Grantham's Distance difference D for each pair of amino acid i and j were compared with both Methionine and Lysine. Those amino acids were considered for replacement which had least Distance difference D with respect to Methionine and Lysine respectively. The substrate binding site, metal binding site and active site of RuBisCo amino acid sequence were not disturbed during modification of the native RuBisCo.

Four Rbcl amino acid sequences of RuBisCo were modified, SEQ ID No. 2 and 3 for Methionine and SEQ ID No. 4 and 5 for Lysine. The modified amino acid sequences were examined through the online Swiss-Model for homologous protein modeling and sequence identity.

In Swiss-Model, GMQE (Global Model Quality Estimation) and QSQE (quaternary structure quality estimate) score is expressed as a number between 0 and 1, reflecting the expected accuracy, reliability, and the reliable quaternary structure prediction in the modelling process respectively. During modification of the amino acid sequences, GMQE & QSQE scores were optimized to near "1" because a score above 0.7 can be believed reliable.

The modified Rubisco nucleotide sequences were codon optimized from the online GenScript Codon Optimization tool. The engineered and codon optimized RuBisCo nucleotide sequences were synthesized from Twist Bioscience, Gene Synthesis Company, San Francisco, Calif., USA.

A construct was designed to replace the native RbcL gene along with its promoter with the native promoter and the variant RbcL genes. 400 bp from upstream flanking region (UFR) and downstream flanking region (DFR) were inserted to integrate the construct into genomic DNA of host strain through homologous recombination.

All cloning was conducted using circular polymerase extension cloning (CPEC) method. All forward and DFR-R reverse primers were designed with 25 to 30 base pair overhang region.

Upstream flanking region (UFR) and downstream flanking region (DFR) were amplified from Genomic DNA of *Synechocystis* Sp. PCC 6803 with UFR-F, UFR-R, DFR-F & DFR-R primers respectively. Kanamycin resistance cassette was used as a selection marker, and was amplified from pEERM3 vector with KmR-F and KmR-R primers.

Native PrbcL promoter was used for expression of engineered RuBisCo protein and was amplified from genomic DNA of PCC 6803 with PrbcL-F and PrbcL-R primers. Engineered RuBisCo nucleotide sequences were amplified with RbcL-F and RbcL-R primers from synthetic pET21 plasmid (Twist Biosience, San Francisco, USA). pUC19 plasmid was used as backbone vector, EcoRI restriction enzyme was used to make it linear a DNA fragment.

In a first step, amplified fragments UFR, KmR and PrbcL with overhang region were combined together by performing SOE PCR. In a second step RbcL and DFR amplified fragments with overhang region were combined together by performing SOE PCR. In a final step 3 the product of step 1 and step 2 along with pUC19 backbone with overhang region were joined together in a single tube one step PCR reaction by the Circular Polymerase Extension Cloning (CPEC) method. pMFO1, pMF02, pMF03 & pMF04 (Corresponding to SEQ ID Nos. 2-5) were constructed by following step (1-3).

Introduction of the plasmid into the cells can be done by electrochemical poration, particle bombardment, detergent-mediated transfection, or related techniques.

Example 2

All of the constructed plasmid pMFO1, pMF02, pMF03 & pMFO4 were transformed in to already prepared chemically competent *E. coli* DH5 alpha cells.

The transformed cells were spread on LB agar plates with carbenicillin 100 μg/ml and incubated overnight at 37° C. The colonies on LB agar plates were screened by colony PCR. The positive colonies for plasmid were inoculated into LB liquid medium with carbenicillin 100 μg/ml.

The pMFO1, PMF02, pMF03 & pMF04 plasmids were purified from DH5 alpha cell liquid culture. The transformed cells were spread on LB agar plates with carbenicillin 100 μg/ml and incubated overnight at 37° C.

The colonies on LB agar plates were screened by colony PCR. The positive colonies for plasmid were inoculated into LB liquid medium with carbenicillin 100 μg/ml.

The pMFO1, PMF02, pMF03 & pMF04 plasmids were then purified from transformed DH5 alpha cell liquid culture. The wild type strains of *Synechocystis* Sp. PCC6803 were grown in BG11 medium and incubated at the standard culture condition (at 30° C., with 100 μE m-2 s-1 of constant illumination).

50 mL of *Synechocystis* Sp. PCC6803 culture with OD of 1 was centrifuged at 8000 RPM for 5 minutes and the pellets were dissolved in fresh BG11 liquid media and were mixed well. The culture was centrifuged again at 8000 RPM for 5 minutes. The pellets were dissolved again in 4 mL of fresh BG11 liquid media and 1 mL of culture was distributed into 4 sterile 1.7 ml tubes. The culture tubes were centrifuged again at 8000 RPM for 5 minutes and the pellets were dissolved in to 400 μL fresh BG11 liquid media.

Then 1 μg of plasmid DNA (pMF01, pMF02, pMF03 & pMF04) was added into each tube respectively and incubated for 6 hrs at 30° C. with shaking at 250 rpm & 100 μEm-2 s-1 of constant illumination. After 6 hrs of incubation the entire 400 μl transformed cells culture were spread on BG11 agar plates with 20 μg/ml of Kanamycin. These plates were incubated at 30° C. with 100 μEm-2 s-1 of constant illumination.

Figure 5:
FIG. 5 is a photo of agar plates after the transformation of example plasmids into WT *Synechocystis* sp. PCC 6803.

FIG. 5 shows two agar plates after the transformation of plasmids pMF01, pMF02, pMF03 & pMF04 into WT *Synechocystis* sp. PCC 6803 as described above.

Example 3

After 7 to 8 days of transformation, the colonies of RuBisCo variant *Synechocystis* Sp. PCC6803 appeared on BG 11 agar plates with 20 mg/ml of Kanamycin. To confirm the constructs, 10 colonies from each of four BG11 agar plates were selected and screened by colony PCR with UFR-F and DFR-R primers. Subculture 1: 8 positive colonies of RuBisCo variant *Synechocystis* Sp. PCC6803 from each LB agar plate were further subcultured on fresh BG11 agar plates with 20 μg/ml of Kanamycin.

These "Subculture 1" plates were further subcultured on fresh BG11 agar plates 20 μg/ml of Kanamycin for several rounds to properly segregate the mutant RbcL gene into the genomic DNA of *Synechocystis* Sp. PCC6803 through homologous recombination.

Selected positive colonies were subcultured on fresh BG11 agar plates with 20 μg/ml of Kanamycin for a total of 7 times and repeated after every two days.

Figure 6:
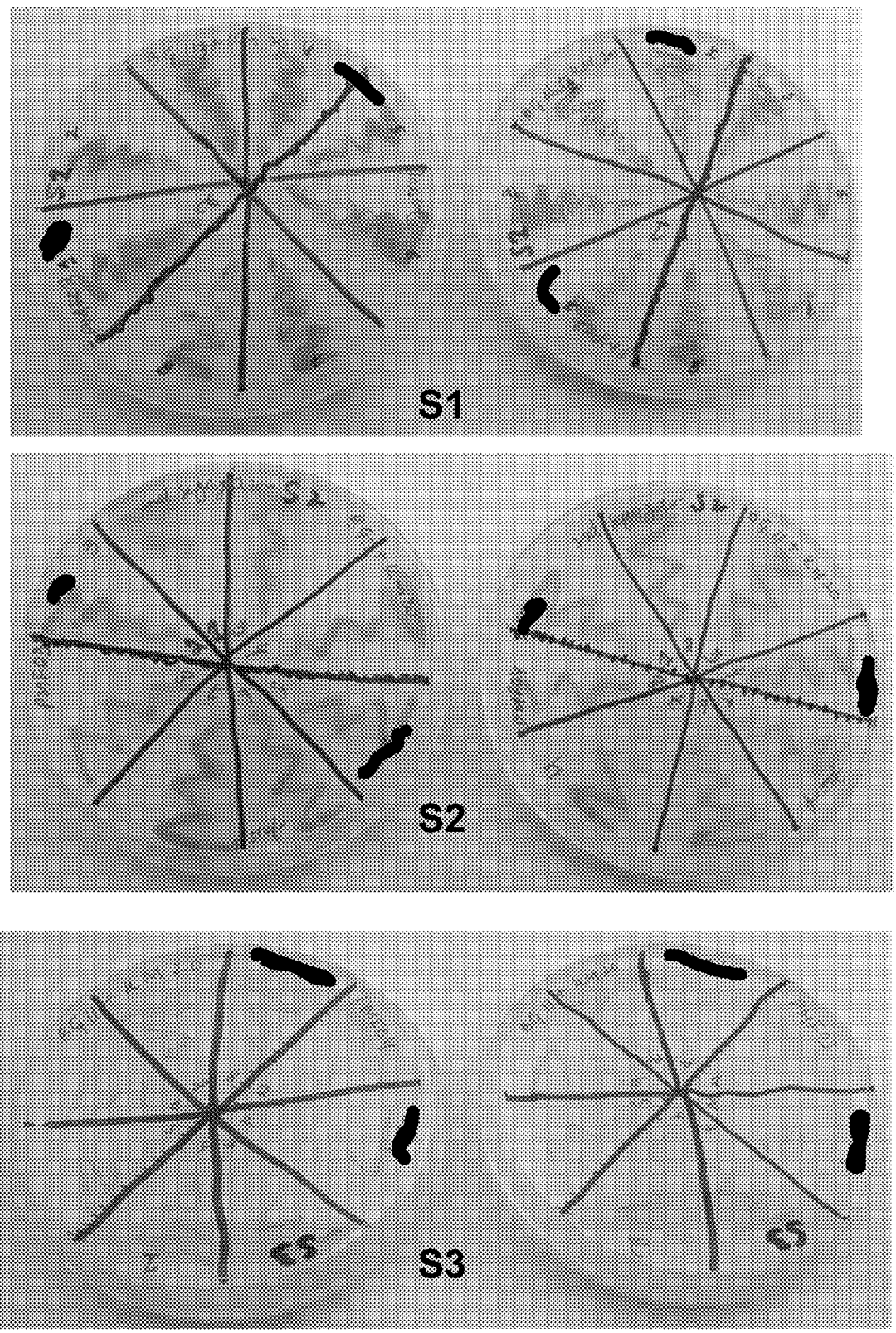
FIG. 6 is a photo showing agar plates with transformed colonies (from Example 5) for segregation.
Figure 7:
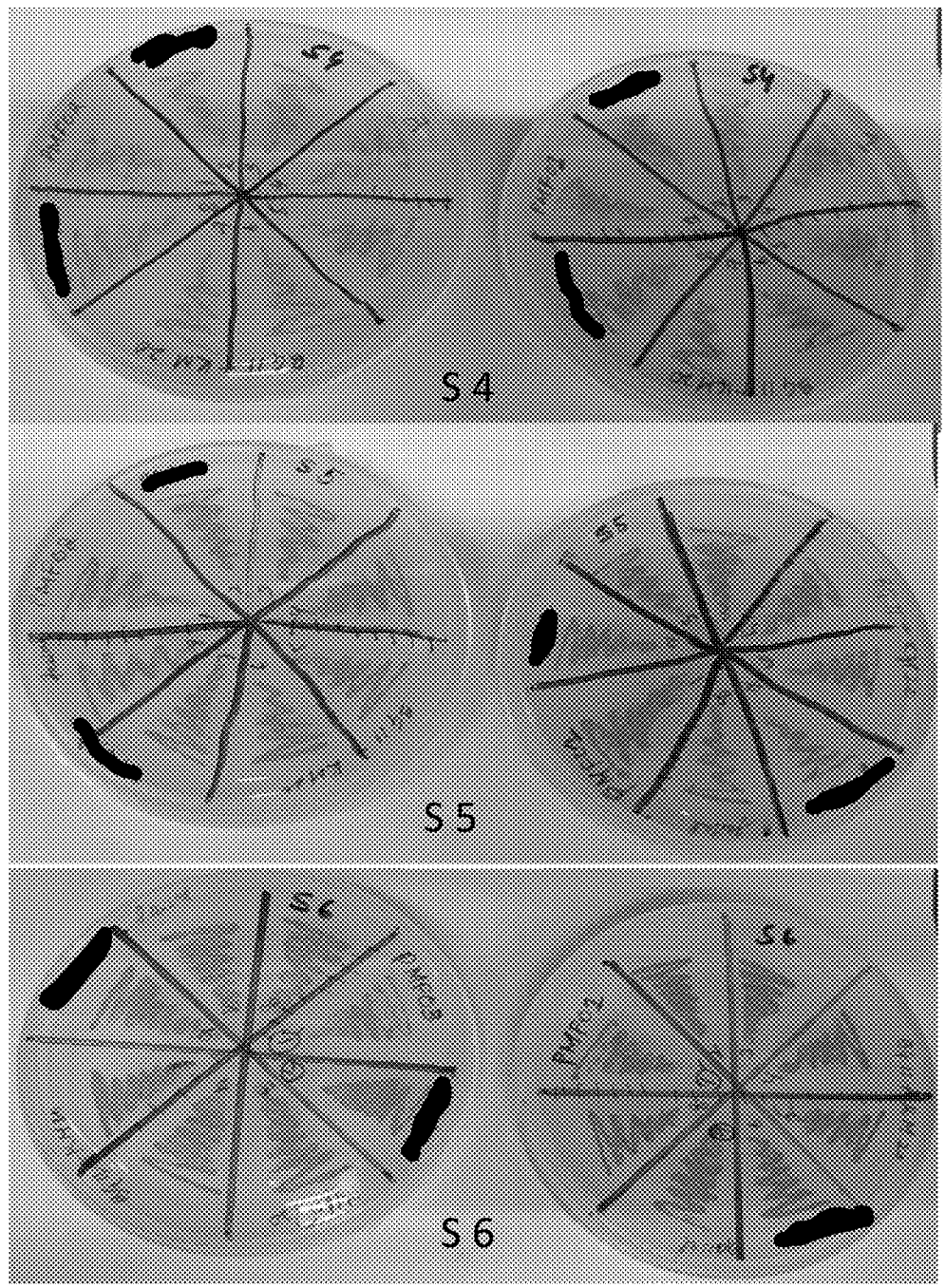
FIG. 7 is a photo showing additional agar plates with transformed colonies (from Example 5) for segregation.

FIGS. 6 and 7 show agar plates with six subcultures with transformed colonies (from Example 3) onto BG11+KM 20 plates for segregation. The stable growth of the cultures indicates nucleus and plastid integration.

TABLE 1

| Transformation | Day 1 |
|---|---|
| Subculture S 1 | Day 9 |
| Subculture S 2 | Day 12 |
| Subculture S 3 | Day 15 |
| Subculture S 4 | Day 17 |
| Subculture S 5 | Day 19 |
| Subculture S 6 | Day 22 |

Example 4

Figure 8:
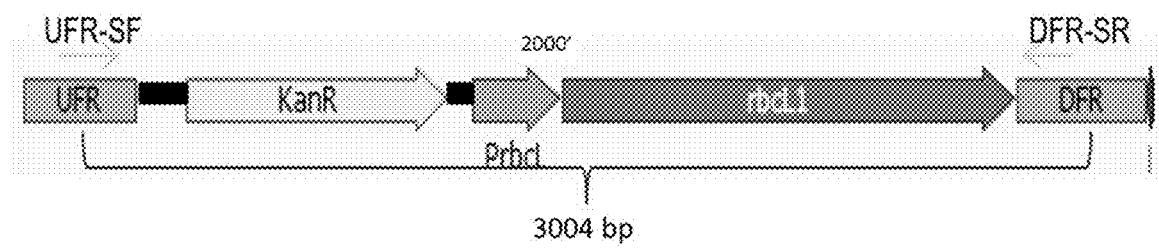
FIG. 8 shows the design that was integrated into the Rbcl loci in *Synechocystis* 6803.

FIG. 8 at the shows the design that was integrated into the Rbcl loci in *Synechocystis* 6803. The presence of antibiotic resistance marker makes the region in between the UFR and DFR to be larger than the region present in the wild-type. The bottom pane shows a gel electrophoresis of the colony PCR for Subculture 6 versus a positive control. Primers binding to the UFR and DFR region of the plasmid were taken and the DNA region in between amplified by PCR and analyze by gel electrophoresis. Presence of bands the same size as that of positive control indicated successful genome integration of pMF01, pMF02, pMF03, and pMF04 RbcL (corresponding to SEQ ID Nos 2-5, respectively).

Example 5

The wild type and RuBisCo variant strains of *Synechocystis* Sp. PCC6803 were grown in 20 mL of BG11 liquid medium with and without 20 μg/ml of Kanamycin, and incubated at the standard culture conditions (30° C., 250 rpm shaking & 100 μE m$^{-2}$ s$^{-1}$ of constant illumination).

RuBisCo variant transformed *Synechocystis* Sp. PCC6803 cells were pellet down from 20 mL of culture at OD 0.8 to 0.9, washed with 0.9% NaCl or water (centrifuged at 19000 g for 8 min, abandon the supernatant) and the pellets were resuspended into 1 ml Eppendorf tubes.

After the cells were transferred in to GC vials, 1.5 ml 6 M HCl was added to the GC vials, the vials were capped and placed in an oven at 100° C. for 24 hours to hydrolyze all of the protein into their amino acid monomers. After 24 hrs incubation, the GC vials were centrifuged at 19000 g for 8 min, the supernatant was kept, and pellets were discarded. The lids of the vials were removed and the samples were dried completely under a steam of air or nitrogen overnight.

The samples were then dissolved with 150 ul of tetrahydrofuran (THF) and 150 µl of n-tetrabutyldimethylsilyl derivatization reagent and were incubated at 60° to 85° C. for 1 hour in an oven or water bath. The samples were centrifuged at 19000 g for 10 minutes and then the supernatant was transferred into new GC vials.

At an injection ratio of 1:5 or 1:10, the following GC MS temperature program was used: hold at 150° C. for 2 min; increase at 3° C. per minute to 280 C; increase at 20° C. per min to 300° C. and hold for 5 minutes.

An analysis of the strain (whole cell comparison) was conducted compared to wild type (WT) RuBisCo in *Synechocystis* (species PCC 6803). The RbcL of the WT corresponded to SEQ ID No. 1.

Figure 9:
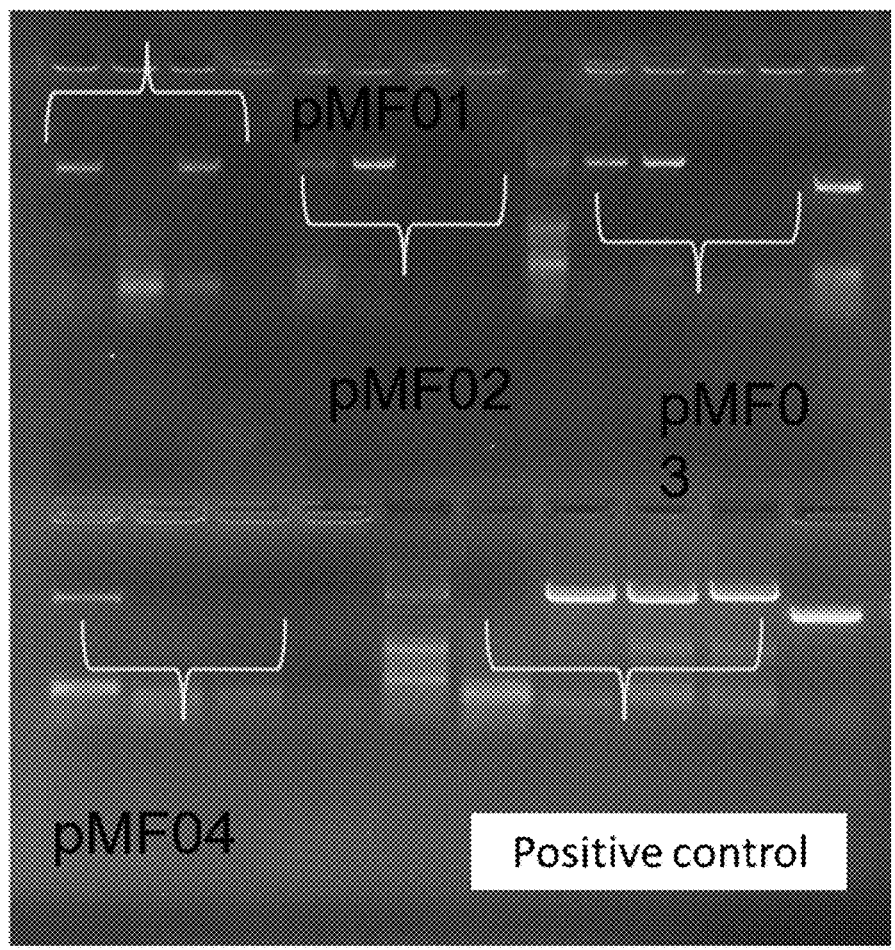
FIG. 9 is a photo showing a GC-MS amino acid analysis of the pMF01 and pMF02 samples (Met replacements top panel); and pMF03, and pMF04 samples (Lys replacements, bottom panel).

FIG. 9 shows a GC-MS amino acid analysis of the pMF01 and pMF02 samples (Met replacements top panel); and pMF03, and pMF04 samples (Lys replacements, bottom panel). The A at the end of the sample IDs in the figures denotes a biological replicate.

Figure 10:
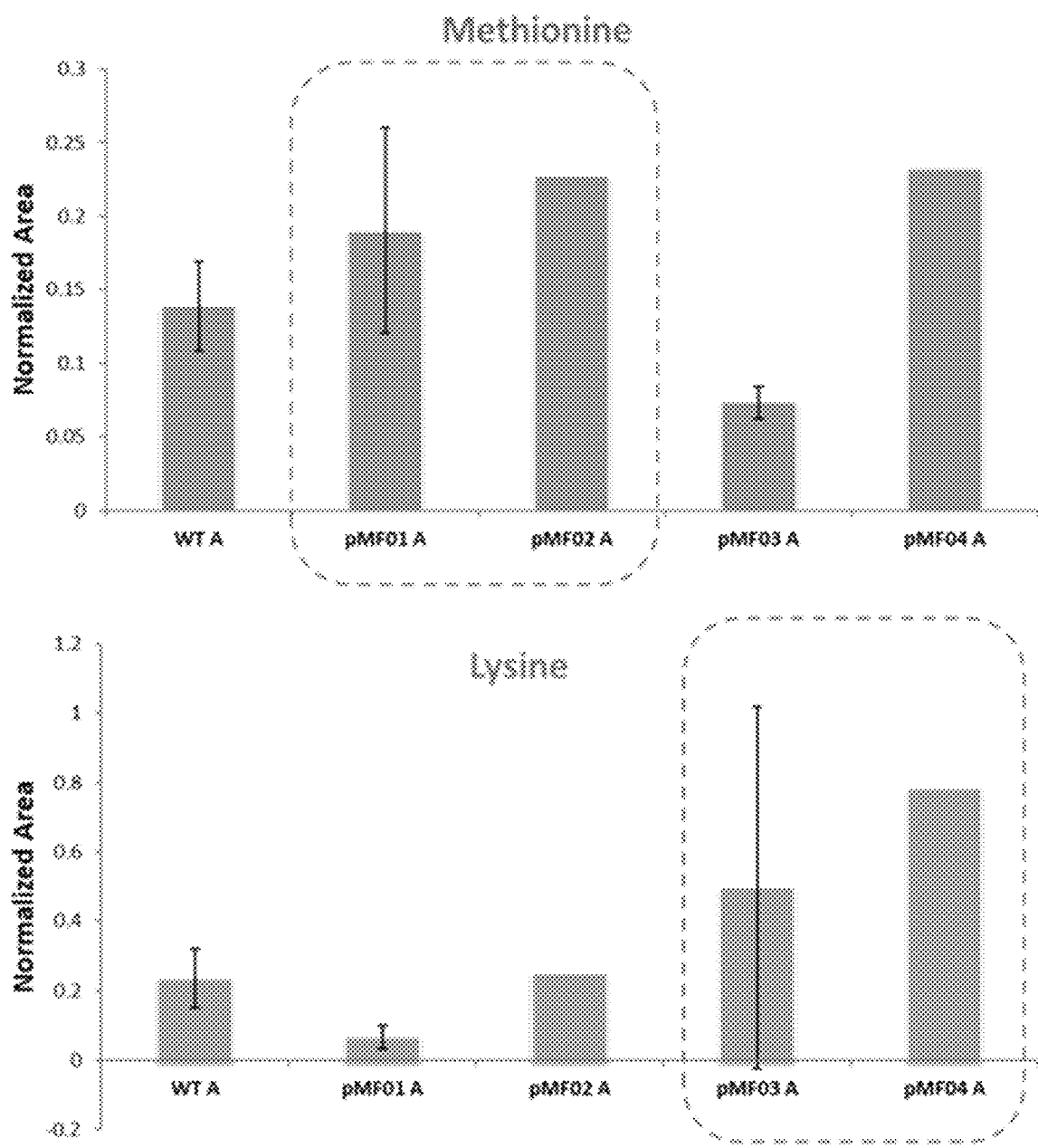
FIG. 10 is a graph showing the significant improvement in the amount of Methionine and Lysine in the example modified RuBisCo compared to the wild type.

FIG. 10 indicates that significant improvement in the amount of Methionine and Lysine in the example modified RuBisCo was accomplished compared to the wild type.

Protein scores were performed on the Example modified RuBisCos, and these were greater than 100, up to about 120, assuming no changes in digestibility.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used.

What is claimed is:

1. A biological material comprising: an amino acid sequence having at least 84% sequence identity to any one of SEQ ID NOS: 2-5; wherein the amino acid sequence is a modified RbcL unit incorporated in a modified ribulose-1, 5-bisphosphate carboxylase/oxygenase; and the modified RbcL unit has relative to SEQ ID NO: 1 substitution of 1 to 30 Leu, Phe, Val or Ile amino acid residues of SEQ ID NO: 1, or combinations thereof, substituted to Met; the modified RbcL unit has relative to SEQ ID NO: 1 substitution of 4 to 35 Arg, Thr, or His amino acid residues of SEQ ID NO: 1, or combinations thereof, substituted to Lys; or the modified RbcL unit has relative to SEQ ID NO: 1 both substitution of 1 to 30 Leu, Phe, Val or Ile amino acid residues of SEQ ID NO: 1, or combinations thereof, substituted to Met and substitution of 4 to 35 Arg, Thr or His amino acid residues of SEQ ID NO: 1, or combinations thereof, substituted to Lys, wherein the modified RbcL unit is enriched in Met amino acid residues relative to SEQ ID NO: 1, enriched in Lys amino acid residues relative to SEQ ID NO: 1, or enriched in both Met and Lys amino acid residues relative to SEQ ID NO: 1.

2. The biological material of claim 1, wherein the amino acid sequence is identical to any of SEQ ID NOS: 2-5 having a sequence length of 440 to 475 units amino acid residues.

3. The biological material of claim 1, wherein the modified RbcL unit is incorporated in a plastid.

4. A biological material of claim 1, wherein the biological material is a biomass.

5. The biological material of claim 4, wherein the biomass comprises *E. coli*.

6. The biological material of claim 4, wherein the biomass is a photosynthetic cyanobacterial biomass.

7. The biological material of claim 6, wherein the biomass comprises *Synechocystis*.

8. The biological material of claim 1, wherein the amino acid sequence has at least 95% sequence identity to any one of SEQ ID NOS: 2-5.

9. The biological material of claim 1, wherein the modified RbcL unit has relative to SEQ ID NO: 1 substitution of 1 to 30 Leu, Phe, Val or Ile amino acid residues of SEQ ID NO: 1, or combinations thereof, substituted to Met.

10. The biological material of claim 1, wherein the modified RbcL unit has relative to SEQ ID NO: 1 substitution of 4 to 35 Arg, Thr, or His amino acid residues of SEQ ID NO: 1, or combinations thereof, substituted to Lys.

11. The biological material of claim 1, wherein the modified ribulose-1,5-bisphosphate carboxylase/oxygenase is a complete protein source for human nutrition.

12. The biological material of claim 1, wherein the modified RbcL unit has relative to SEQ ID NO: 1 substitution of 14 to 25 Leu, Phe, Val or Ile amino acid residues of SEQ ID NO: 1, or combinations thereof, substituted to Met.

13. The biological material of claim 1, wherein the modified RbcL unit has relative to SEQ ID NO: 1 substitution of 20 to 30 Arg, Thr, or His amino acid residues of SEQ ID NO: 1, or combinations thereof, substituted to Lys.

14. A method for producing a modified RbcL unit of a ribulose-1,5-bisphosphate carboxylase/oxygenase, comprising:

transforming a host cell with a plasmid encoding the modified RbcL unit, and culturing the transformed host cell to produce the modified RbcL unit;

wherein the modified RbcL unit comprises an amino acid sequence having at least 84% sequence identity to any one of SEQ ID NOS: 2-5, wherein the modified RbcL unit has relative to SEQ ID NO: 1 substitution of 1 to 30 Leu, Phe, Val or Ile amino acid residues of SEQ ID NO: 1, or combinations thereof, substituted to Met; the modified RbcL unit has relative to SEQ ID NO: 1 substitution of 4 to 35 Arg, Thr, or His amino acid residues of SEQ ID NO: 1, or combinations thereof, substituted to Lys; or the modified RbcL unit has relative to SEQ ID NO: 1 both substitution of 1 to 30 Leu, Phe, Val or Ile amino acid residues of SEQ ID NO: 1, or combinations thereof, substituted to Met and substitution of 4 to 35 Arg, Thr or His amino acid residues of SEQ ID NO: 1, or combinations thereof, substituted to Lys, and wherein the modified RbcL unit is enriched in Met amino acid residues relative to SEQ ID NO: 1, enriched in Lys amino acid residues relative to SEQ ID NO: 1, or enriched in both Met and Lys amino acid residues relative to SEQ ID NO: 1.

15. The method of claim 14, wherein the host cell is a photosynthetic cyanobacterial cell.

16. The method of claim 15, wherein the host cell is *Synechocystis*.

17. The method of claim 14, wherein the host cell is *E. coli*.

* * * * *